US006561973B1

(12) United States Patent
Bala

(10) Patent No.: US 6,561,973 B1
(45) Date of Patent: May 13, 2003

(54) MICRO-ENDOSCOPIC SYSTEM

(76) Inventor: John L. Bala, 80 Covell Rd., Pomfret Center, CT (US) 06259

( * ) Notice: Subject to any disclaimer, the term of this patent is extended or adjusted under 35 U.S.C. 154(b) by 88 days.

(21) Appl. No.: 09/625,425

(22) Filed: Jul. 25, 2000

(51) Int. Cl.[7] .............................. A61B 1/07; A61B 1/04
(52) U.S. Cl. ...................... 600/178; 600/182; 600/168; 600/160; 600/131; 600/130
(58) Field of Search .................. 600/112, 130, 600/136, 178, 180–182, 131, 172, 476, 478, 168; 359/434, 435; 385/116, 117

(56) References Cited

U.S. PATENT DOCUMENTS

| | | | | |
|---|---|---|---|---|
| 5,213,092 A | * | 5/1993 | Uram | 600/156 |
| 5,309,330 A | * | 5/1994 | Pillers et al. | 362/574 |
| 5,419,313 A | * | 5/1995 | Lemke | 600/133 |
| 5,617,498 A | * | 4/1997 | Cawood | 385/117 |
| 5,887,965 A | * | 3/1999 | Edens et al. | 362/276 |
| 5,889,370 A | * | 3/1999 | Arai et al. | 315/248 |
| 5,892,630 A | * | 4/1999 | Broome | 359/656 |
| 6,201,989 B1 | * | 3/2001 | Whitehead et al. | 600/476 |
| 6,212,425 B1 | * | 4/2001 | Irion et al. | 600/476 |

\* cited by examiner

*Primary Examiner*—John P. Leubecker
(74) *Attorney, Agent, or Firm*—Alix, Yale & Ristas, LLP

(57) ABSTRACT

A micro-endoscopic system employs a pulsed xenon light source and image collection optics with a fine diameter optical probe for an endoscope. Very bright pulses of light emitted by a xenon flash tube increase the intensity of light incident on the light transmitting optics, allowing a reduction in size of the optical components, resulting in a corresponding reduction in the size of the optical probe. A segmented glass image guide directs the reflected light to a sensor array. Segmentation of the image guide avoids the stress related problems associated with fine diameter glass optical structures.

19 Claims, 7 Drawing Sheets

MICRO-ENDOSCOPIC SYSTEM

BACKGROUND OF THE INVENTION

1. Field of the Invention

This invention relates to endoscopes which are widely used in the field of medicine and in particular to a compact endoscope having a fine diameter probe for use in hospitals and doctors' offices for outpatient procedures.

2. Description of the Related Art

Currently, orthopaedic surgeons perform the greatest number of arthroscopic in-hospital procedures, approximately half of which could be performed on an outpatient basis. Almost 2.5 million such procedures are undertaken annually. Of these, 510,000 are for shoulder injuries, 1.7 million are for knee injuries, and 200,000 are for such procedures as elbows, ankles and wrists. The future arthroscopic market is expected to be additionally enhanced by anticipated developments in the fields of synthetic bone and tissue transplantation.

Currently available endoscopes have the disadvantages of being bulky, expensive instruments which are typically found only in hospitals. Available endoscopes have relatively large diameter optical probes, requiring proportionately large incisions to permit their use. There is a need in the art for a compact, small diameter endoscope, which may be purchased and used by medical professionals in their offices to perform outpatient diagnostic and surgical procedures.

There are at least two major technical obstacles to the design of an endoscope having an outside diameter of less than 2 mm. The first obstacle is that of insufficient illumination. An endoscope must both provide light to the area within the body being viewed and collect sufficient reflected light to be detected by available sensor arrays. The narrow optical pathways available in a very small diameter endoscope have typically not been capable of transmitting or collecting sufficient light.

The quantity of light transmitted in any optical arrangement is principally determined by two factors: 1) the optical characteristics of the light receiving surface of the arrangement (surface area, curvature, etc.); and 2) the intensity of the light energy incident upon that surface. Reduction in either factor reduces the amount of light transmitted.

In conventional endoscopic systems, these transmission constraints restrict the ability to effectively reduce the diameter of the probe which delivers light into the cavity to be viewed and collects the reflected image. Light sources of conventional brightness are not compatible with optical transmission systems which employ a significant reduction in the surface area of the light transmission pathway. Accordingly, there is a need in the art for an endoscopic system which can deliver sufficiently intense light energy to an endoscope to permit reduction in the light transmission portion of an endoscope probe.

Collection of the reflected light which will form an image of the viewing area presents another set of technical difficulties. Prior art endoscopes typically focus the image on either a charge coupled device (CCD) sensor array or magnify the image into an eye piece that the surgeon or medical professional can view directly. Ideally, a single glass rod could be used to transmit image light from an object lens to the sensor array. Such a construction is employed in many larger diameter conventional endoscopes. However, as the diameter of such a glass rod is reduced, the rod becomes vulnerable to stress induced birefringence, which distorts the image being transmitted.

Conventional optical fibers, while they are thin enough to be flexible and avoid the problem of birefringence, have cross sectional surface areas which individually collect only limited amounts of light. No matter how many such fibers are used, the brightness of the transmitted image is not enhanced because the optical characteristics of the receiving or input face of each fiber do not change. Thus, there is also a need in the art for a fine diameter endoscope probe which uses a single optical pathway to collect and deliver image light to a suitable sensor array.

SUMMARY OF THE INVENTION

Briefly stated, the invention in a preferred form comprises a compact, office-based fine diameter endoscope system which employs a pulsed xenon light source and novel image delivery optics to provide an endoscope probe having a diameter which is reduced in comparison to comparable conventional probes. The micro-endoscope system (ME system) includes a service module, a combined optical and electronic service cable and a micro-endoscopic device (MED). The service module houses the system power supply, the pulsed xenon light source, the image processor and the control electronics as well as the display/monitor. The combined optical and electronic cable contains a fiber optic bundle to transmit light from the service module to the MED and conductors to communicate with the electronic portion of the MED.

The MED comprises a sensor head that contains a sensitive charge coupled device (CCD) sensor array, a light pulse transfer interface and image focus optics. Controls allow the user to control the focus and magnification functions. A removable, one-piece optical probe and ergonomic grip slides over the sensor head to mate with the light pulse transfer interface. The optical probe includes a light pipe to deliver light from the pulse transfer interface to the viewing area and an image path for collecting and guiding reflected light back to the image focus optics. The pulse transfer interface enhances the transfer of light from the fiber optic bundle to the light pipe. Light travels the length of the light pipe and is directed upon the area to be viewed. Light reflected from the viewing area is collected by an object lens and focused into the image path. The image path guides reflected light to the image focus optics in the sensor head where the image is focused on the CCD array. Image data from the CCD array is communicated to the service module electronics through the service cable.

To enhance the intensity of light incident on the optical components of the light path, the MED utilizes a pulsed xenon light source which emits short duration, very high-energy pulses of light. Each pulse of light may be in the energy range of 100,000 watts and have a duration of approximately 10 microseconds. The pulsed xenon light source is essentially a point source of light. The pulsed xenon light source is positioned so the emitted pulses of light pass directly into the input end of the fiber optic bundle. The highly concentrated light energy provides sufficient illumination of the viewing area while employing a smaller diameter light path.

Image path optics having a diameter of approximately 1 mm address the issue of birefringence by using an image guide comprised of glass rod segments. Short rod segments are not prone to the stresses which induce birefringence. The sections of the image guide are assembled to form an integrated guide having the length desired for the optical probe. An alternate embodiment of the image guide may be constructed of optical grade plastic, such as polyethylene.

An object of the present invention is to provide a new and improved fine diameter endoscope having an efficient and cost effective construction and which is adaptable for use in out-patient clinics and doctors' offices.

Another object of the present invention is to provide a new and improved fine diameter endoscope which employs novel image collection optics to enhance image quality.

A further object of the present invention is to provide a new and improved fine diameter endoscope which uses a novel pulsed xenon light source to increase the illumination of the viewing area.

A yet further object of the present invention is to provide a new and improved fine diameter endoscope which may be used as an inexpensive real-time diagnostic tool.

These and other objects, features, and advantages of the invention will become readily apparent to those skilled in the art from the specification and the accompanying drawings.

DETAILED DESCRIPTION OF THE PREFERRED EMBODIMENT

Figure 1:
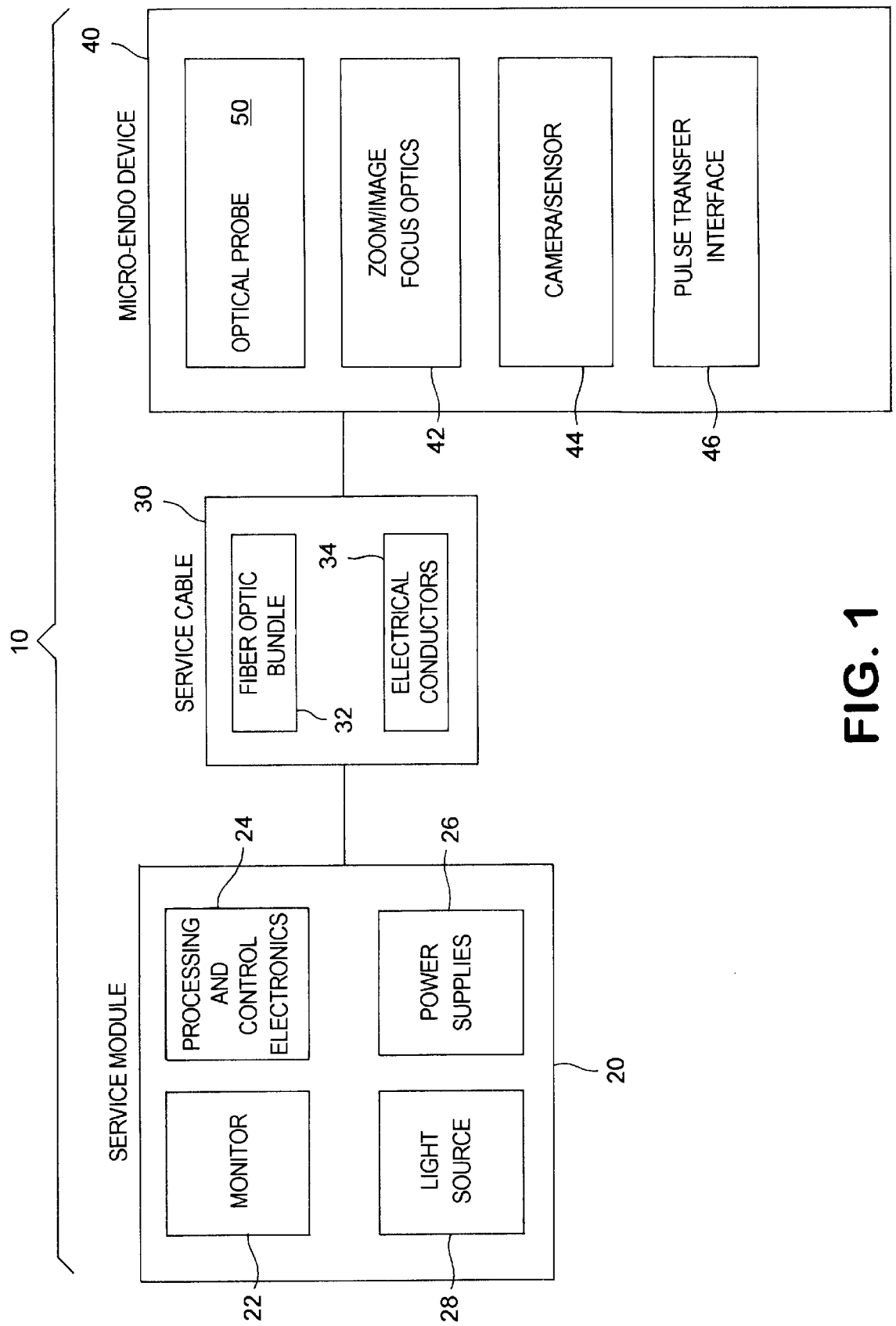
FIG. 1 is a schematic block diagram of a micro-endoscopic system (ME system) in accordance with the present invention.

A micro-endoscopic system (ME system) incorporating a micro-endoscopic device (MED) 40 in accordance with the present invention is generally designated by the numeral 10. With reference to FIG. 1, one embodiment of the ME system is comprised of a service module 20, service cable 30 and a MED 40. The service module 20 contains a video monitor 22, a pulsed xenon light source 28, system power supplies 26 and system processing and control electronics 24.

A service cable 30 connects the service module 20 with the MED 40. The service cable includes a fiber optic bundle 32 to transmit light from the light source 28 to the MED 40. The service cable 30 also incorporates electrical conductors 34 to allow the service module 20 to communicate with the electronic portions of the MED 40. Because of the compact size of the ME system 10, the service cable may be as short as 2 meters. A short service cable 20 increases the amount of light reaching the viewing area by limiting the distance dependent losses associated with transmittal of light through long fiber optic cables. The service cable 20 may be permanently affixed to the service module 20 and MED 40 or may be equipped with couplings at one or both ends to allow removal from the service module 20 and/or the MED 40. A permanent installation has the advantage of eliminating the light losses associated with fiber optic couplings.

Figure 6:
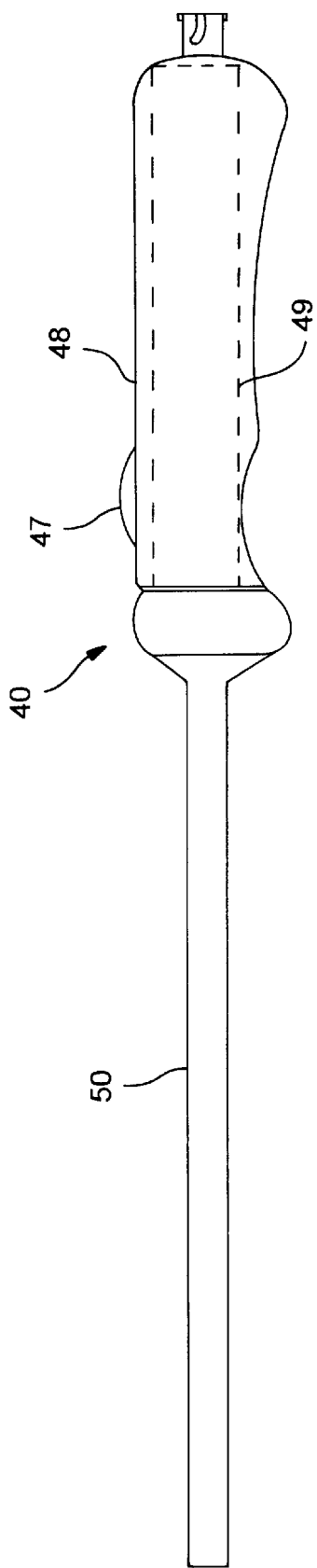
FIG. 6 is a side view of an MED in accordance with the present invention.

The functional components of the MED 40 are illustrated in FIG. 1. The MED 40 comprises an optical probe 50, a sensor head 49 which contains a zoom/image focus optics package 42, a CCD sensor array (which may also be referred to as a camera) 44 and a light pulse transfer interface 46. With reference to FIG. 6, an MED housing 48 is a rigid structure which may be integrally connected to the optical probe 50. In a preferred embodiment, an integrated optical probe 50 and housing 48 slidably mount over the sensor head 49 and lock in place. The housing 48 has a compact hand-held configuration which is exteriorly contoured to fit the hand of a user to facilitate dexterous and versatile usage.

The removable integrated optical probe 50 and MED housing 48 permit replacement of the entire exterior of the MED 40. Once used, the integrated optical probe 50 and MED housing 48 may be replaced with a sterile unit. Probes having alternative magnifications and fields of view are also possible. A removable optical probe/housing allows the MED to be efficiently prepared for the next patient by simply replacing a used probe with a new probe/housing. An interchangeable probe/housing also allow the physician to easily alter the field of view.

Figure 2:
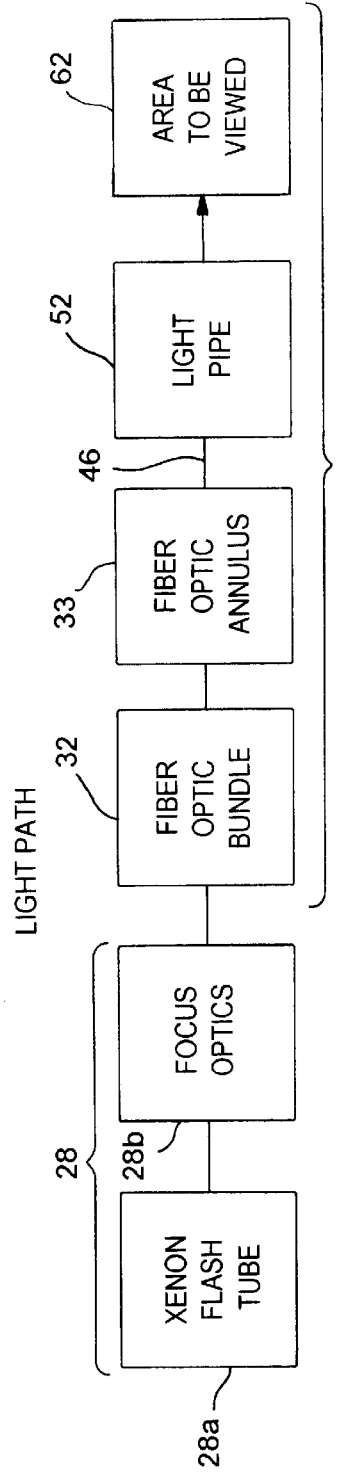
FIG. 2 is a schematic block diagram of the light path for the ME system of FIG. 1.

As illustrated in FIG. 2, the ME system provides a light source 28 and light path 60 which enhance the illumination of the viewing area. The pulsed xenon light source 28 incorporates a flash tube 28a which emits a pulse of light of great intensity and broad spectrum but extremely short duration. The duration of the light source pulses is preferably less than 15 micro-seconds. For example, the flash tube may emit a light pulse having the equivalent of 100,000 watts of light power, but last only 10 micro-seconds. A continuous source of light having this intensity would generate significant and unwanted quantities of heat. The short duration of the light pulses from the flash tube 28a avoids any significant heat buildup. Light generated by the flash tube 28a is focused on the light receiving face of the fiber optic bundle 32 by light focus optics 28b. Light focus optics 28b further enhance the intensity of light incident on the receiving face by gathering, directing and focusing the light.

Figure 14:
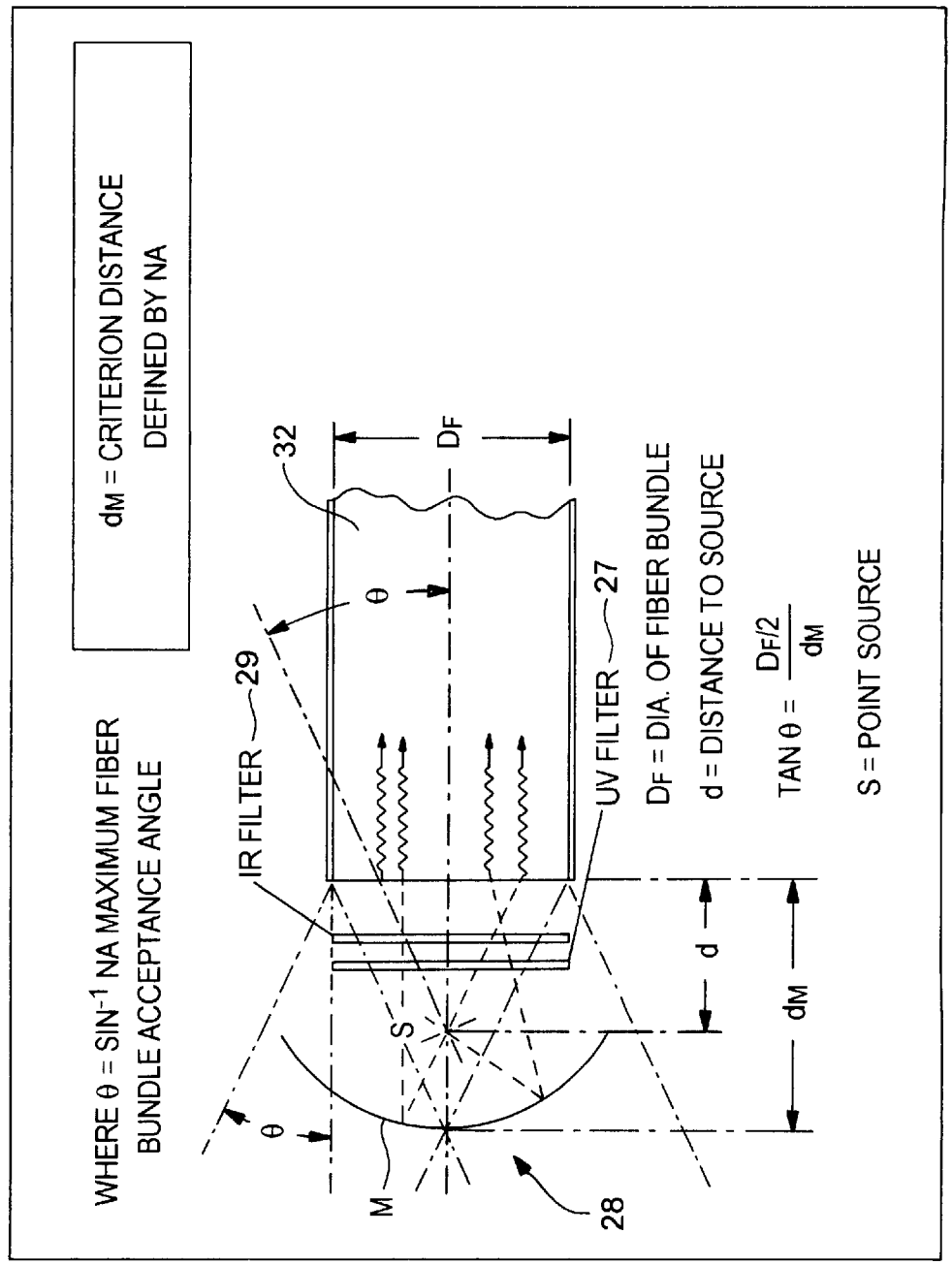
FIG. 14 is a schematic view showing the relationship of the pulsed xenon light source to the light transmitting fiber optic bundle.

FIG. 14 illustrates one embodiment of a light source 28 incorporating a point source xenon flash tube S, focus reflector M, ultra violet filter 27 and infra red filter 29. The maximum fiber bundle acceptance angle $\theta$ of the fiber optic bundle 32 is calculated using the formula $\theta = \sin^{-1} NA$ where NA is the numerical aperture of each fiber. Point source xenon flash tube S is positioned distance d and reflecting mirror M is positioned distance $d_M$ from the light-receiving end of the fiber optic bundle 32. Distances d and $d_M$ are calculated with reference to the maximum fiber bundle acceptance angle θ so that most of the light emitted by point source xenon flash tube S directly incident upon or reflected by mirror M to be incident upon the light receiving end of the fiber optic bundle 32 at an angle of θ or less. This arrangement maximizes the light incident upon the light-receiving end, and ultimately transmitted by the fiber optic bundle 32. Ultra violet filter 27 and infra red filter 29 exclude undesirable portions of the broad spectrum emitted by the flash tube S.

The internal components of the MED are illustrated in FIGS. 6–9. Within the MED 40, the light path comprises the terminus of the fiber optic bundle 32, a pulse transfer interface 46 and a light pipe 52. Light pulses are delivered to the MED via the fiber optic bundle 32 in the service cable 30. Upon entering the sensor head 49, the fiber optic bundle 32 divides into a fiber optic annulus 33. The fiber optic annulus 33 forms the light delivery side of the pulse transfer interface 46. The ring-shape of the fiber optic annulus 33 is optically matched by the circular entrance to the light pipe 52.

Figure 5:
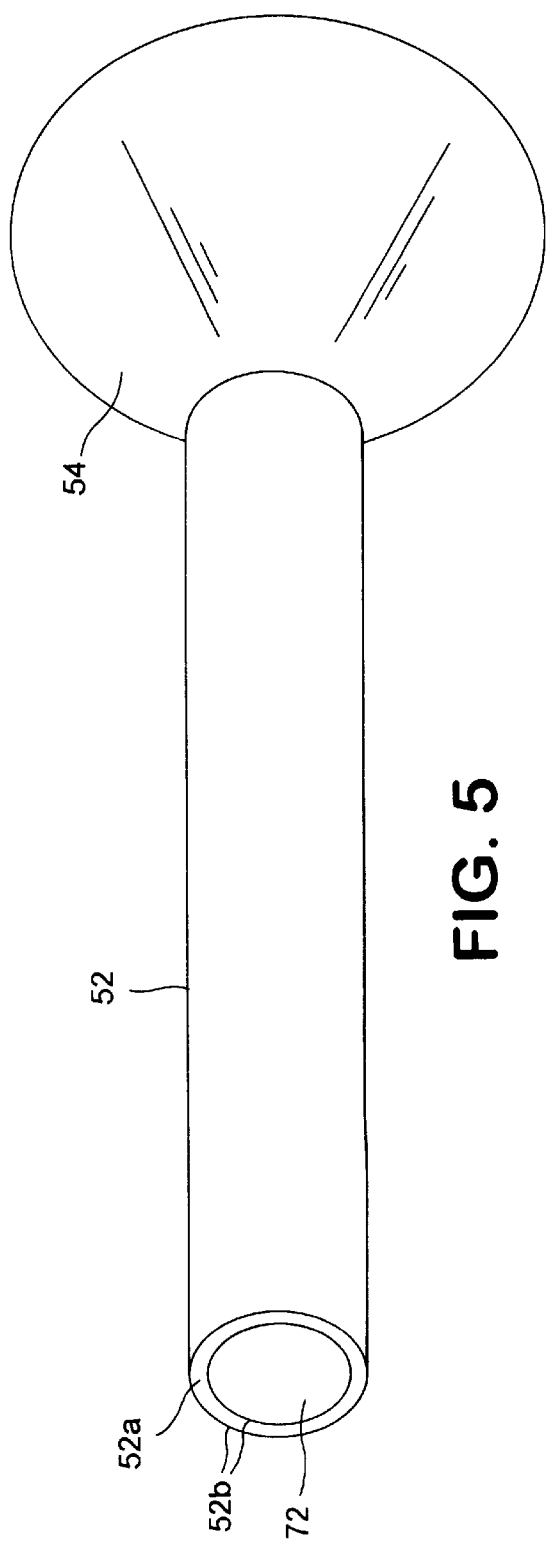
FIG. 5 is an enlarged fragmentary perspective side view of an optical probe of an MED in accordance with the present invention.

The light pipe 52 comprises a core light transmitting material 52a having a high index of refraction surrounded by material having a low index of refraction 52b, thereby creating a light tunnel in a manner similar to the methods used in fiber optics. The light pipe 52 is tubular in shape and surrounds the object lens 72 and the image guide 74. Specifically, the light emitting end of the light pipe 52 is preferably a ring approximately 2 mm in diameter with a wall thickness of 0.1 mm to 0.3 mm (best seen in FIG. 5). The light receiving entrance to the light pipe 52 is a cone 54, expanding from the thin wall tube of the probe portion of the light pipe 52 to a circle which abuts the fiber optic annulus 33 at the pulse transfer interface 46.

FIG. 2 is a schematic representation of the light path 60 from the light source 28 to the area to be viewed. Short duration pulses of broad spectrum light are generated by the xenon flash tube 28a. The light focus optics 28b filter and focus the light onto a light receiving, or input end of the fiber optic bundle 32. The fiber optic bundle traverses the length of the service cable, enters the MED and divides to form the fiber optic annulus 33, or light delivery portion of the pulse transfer interface 46. The cone 54 of the light pipe 52 forms the receiving side of the pulse transfer interface 46. When the integrated optical probe 50 and MED housing 48 are installed over the sensor head 49, the cone 54 and the fiber optic annulus 33 are directly coupled. Light received by the light pipe 52 travels the length of the probe and exits the light pipe 52 to illuminate the viewing area.

Figure 3:
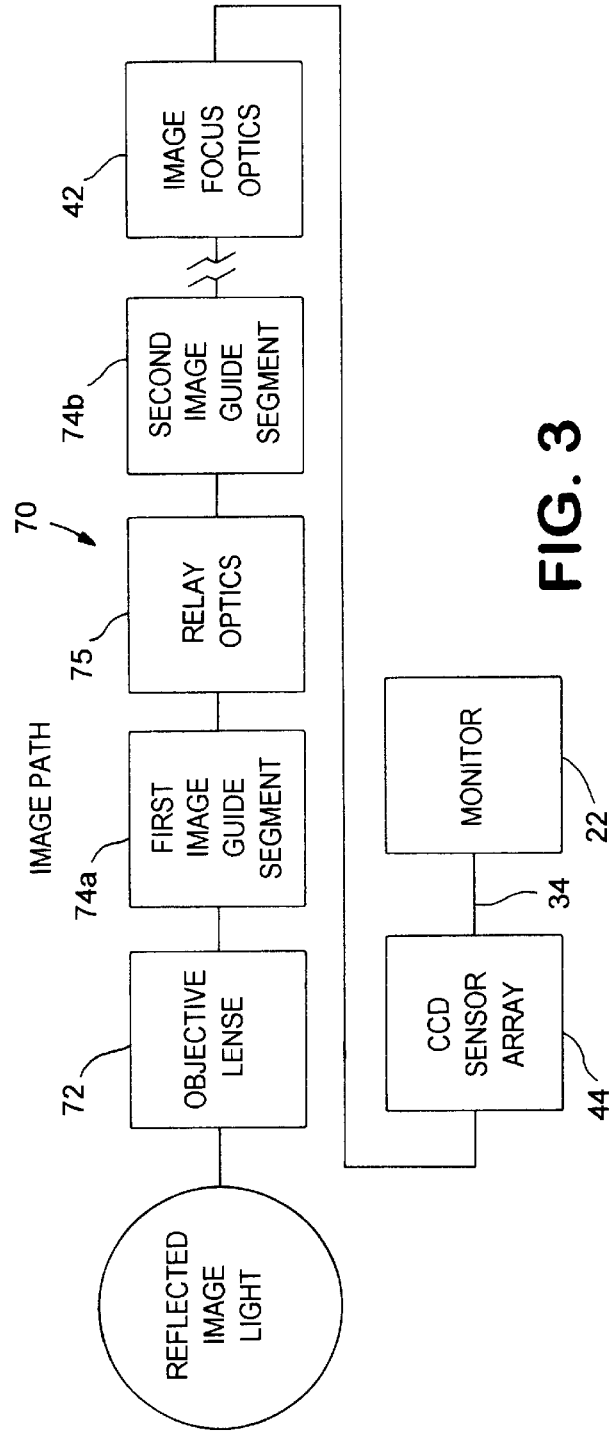
FIG. 3 is a schematic block diagram of the image path for the ME system of FIG. 1.

The ME system also comprises an image path 70 for collecting, guiding, focusing, and displaying the reflected light from which an image of the area being viewed will be constructed. A schematic representation of the ME system image path 70 is found in FIG. 3. Reflected image light is gathered by an objective lens 72 which focuses the light into the first segment 74a of the image guide 74. Relay optics 75 allow the image light to pass from one guide segment 74a to the next 74b without excessive loss or distortion. The image guide segments 74a, 74b, etc. guide the image light to image focus optics 42 where the image light is focused on the CCD sensor array 44. Conductors 34 in the service cable transmit the signals produced by the CCD sensor array 44 to the service module where processing electronics display the image on a monitor 22 for viewing by the physician.

Figure 4:
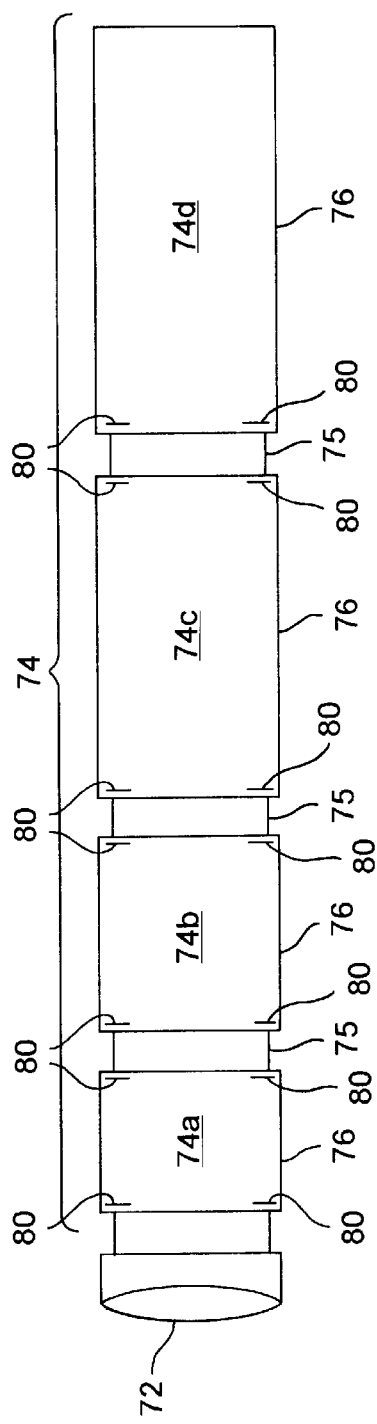
FIG. 4 is an enlarged fragmentary side view of an image guide structure which may be employed in the optical probe of the MED in accordance with the present invention.

The image guide 74 is approximately 1 mm in diameter and must therefore address the issue of birefringence. In one embodiment, the image guide 74 may comprise a segmented glass rod approximately 1 mm in diameter. Breaking the image guide 74 into segments avoids the stresses that induce birefringence in a longer glass rod of this diameter (see FIG. 4). The segments 74a–74d are joined by relay optics 75 which facilitate the transfer of image light from one guide segment to another.

The image guide 74 utilizes reverse fiber optic technology. The outside surface of the guide 74 is coated with light absorbent material 76 to absorb stray light in the image guide. It is desirable to provide the coating to absorb any light which strays from the focused path within the guide to avoid the deleterious effects stray light can have on image quality. Each image path segment may also comprise an aperture stop 80 at the light entry end and at the light transmission end. In combination, the aperture stops 80 and light absorbent coatings 76 ensure that only properly focused image light will be delivered to the image focus optics 42 and in turn the CCD sensor array 44.

The image guide 74 may also be comprised of high quality plastic, such as the optical grade resins used in opthalmic lenses, having an index of refraction in excess of 1.6. The segmenting of a glass rod and the relay optics necessary to transmit an image from one segment to another may be avoided. The somewhat reduced light transmission capability of a plastic material can be compensated for by the increased intensity of light from the pulsed xenon light source.

Figure 10:
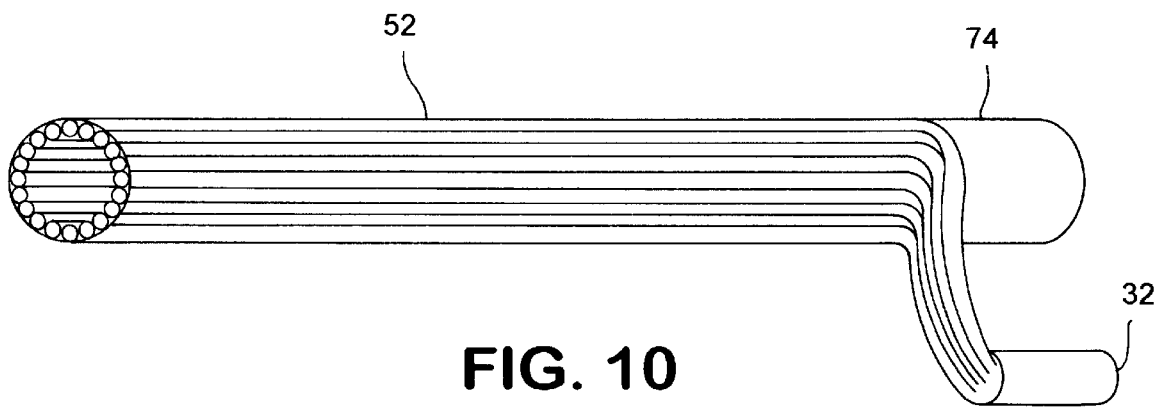
FIG. 10 is a fragmentary perspective side view of an alternative embodiment of the light pipe component of an optical probe for an MED in accordance with the present invention.

The light pipe 52 may be constructed by molding optical quality glass or plastic materials into a unitary piece. FIG. 10 illustrates an alternative configuration for the light pipe 52 incorporating optical fibers formed into a tube surrounding the image guide. In this configuration, the fibers making up the fiber optic bundle 32 are separated and arranged around the image guide 74 in a tubular configuration. The complexity and inefficiencies associated with a pulse transfer interface are thus avoided entirely.

Figure 11:
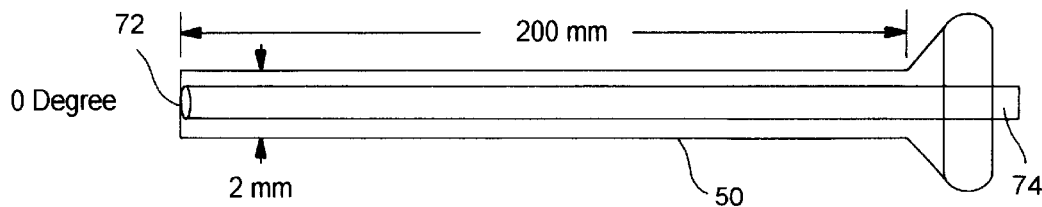
FIG. 11 is a side view, partially in phantom, of the optical probe of the MED of FIG. 6.
Figure 12:
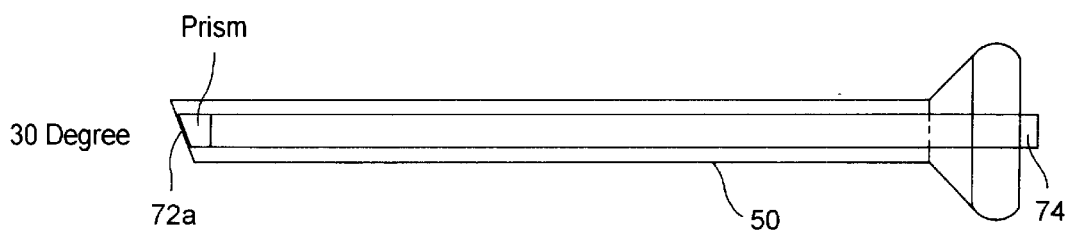
FIG. 12 is a side view, partially in phantom, of an alternative embodiment of an optical probe for use in conjunction with the MED of FIG. 6.
Figure 13:
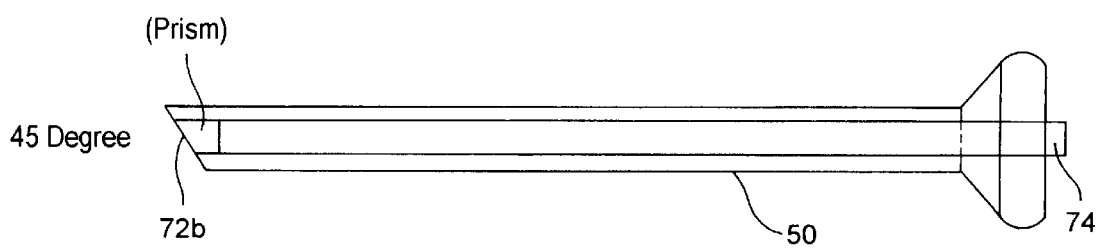
FIG. 13 is a side view, partially in phantom of an alternative embodiment of an optical probe for use in conjunction with the MED of FIG. 6.

FIGS. 11–13 illustrate alternative configurations of the optical probe. FIG. 11 illustrates a probe having an objective lens 72 oriented perpendicular to the length of the probe 50. A probe having this configuration will provide an image of the viewing area directly in front of the objective lens 72. FIGS. 12 and 13 illustrate probes 50 equipped with prisms in their objective lens assemblies 72a, 72b. The angled end face of each probe houses a prism that captures and bends light into the image guide 74. Probes so equipped will give a view of the viewing area angularly offset from the MED. Rotating the MED will allow the physician a panoramic field of view surrounding the location of the MED.

Figure 7:
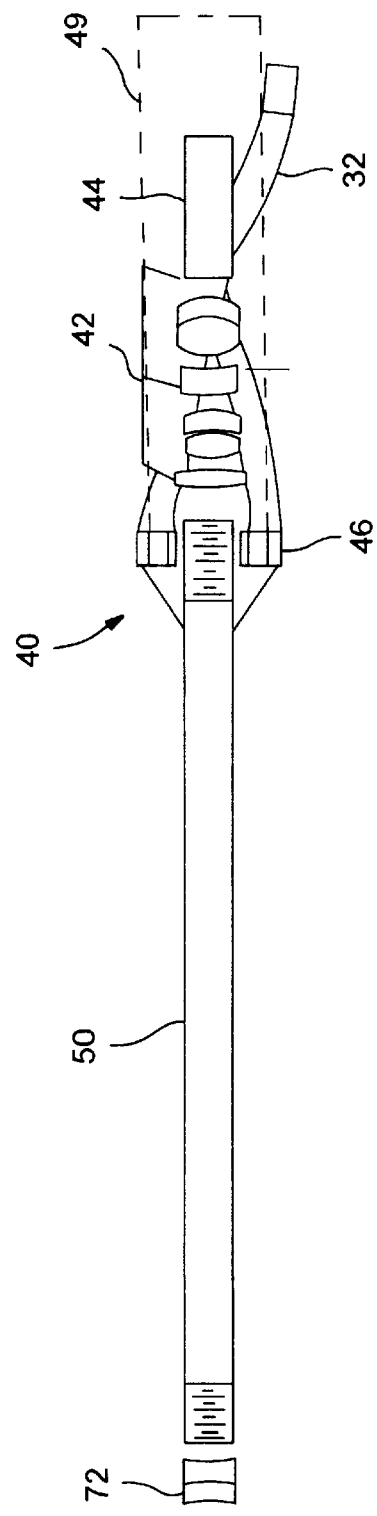
FIG. 7 is a side view, partly broken away, partly in section, and partly in schematic of the MED of FIG. 6.
Figure 8:
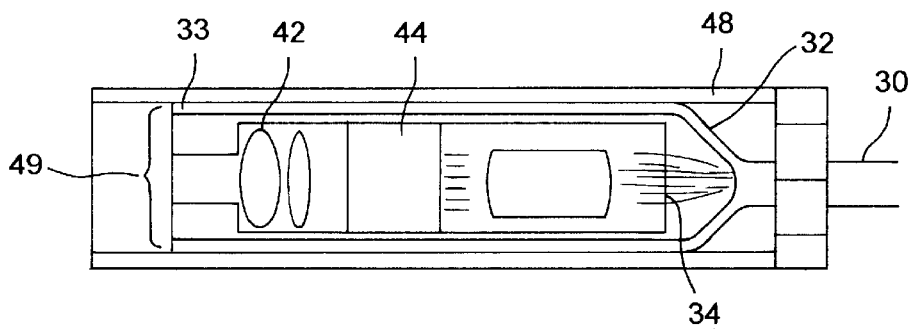
FIG. 8 is a sectional view of the MED of FIG. 6 with the optical probe removed.
Figure 9:
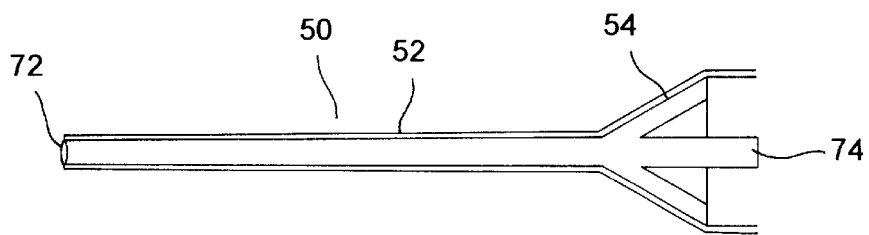
FIG. 9 is a sectional view of the optical probe of the MED of FIG. 6.

FIG. 7 illustrates a zoom/focus optics arrangement which may be incorporated into the MED. Zoom capability allows the physician to get a closer view of the viewing area without having to adjust the physical position of the optical probe 50. This feature is desirable in close quarters or where movement of the probe could possibly damage sensitive tissues. The spacing of lenses 45 in the zoom/focus optics are adjustable by a zoom focus control 47 that permits user selection among multiple zoom positions. The zoom/focus control 47 is provided on the MED housing 48 (see FIG. 6).

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. An endoscope system comprising:
   a light source having a xenon flash tube;
   a light source optical system in optical communication with said light source;
   an optical cable having an input end and an output end, said input end being in optical communication with said optical system;
   a sensor head including a sensor array and an image focus optical system;
   a removable optical probe, said probe having a light pipe for transmitting light received from the output end of said optical cable to an area to be viewed, an object lens for collecting light reflected from said area and an image guide for transmitting said reflected light to a location remote from said area, said probe further comprising a rigid housing, said housing exteriorly contoured for manual grasping, wherein said housing is removably installable over said sensor head;
   means for removably mounting said probe to said housing;
   wherein said xenon flash tube emits a series of light pulses, said light source optical system focuses each said light pulse on said input end and said optical cable conducts said light pulse to said light pipe, said object lens collects said reflected light and said image guide directs said reflected light to said image focus optical system which focuses said light on said sensor array.

2. The endoscope system of claim 1, wherein said image path comprises a glass rod formed of a plurality of segments, each segment being coated with light absorbent material and including an aperture stop.

3. The endoscope system of claim 2, wherein said glass rod has a diameter of approximately 1 mm.

4. The endoscope system of claim 1, wherein said light pipe comprises a tubular structure surrounding said light path, said tubular structure having a thickness of approximately 0.1 mm.

5. The endoscope system of claim 4, wherein said tubular structure is formed by an arrangement of optical fibers, each said optical fiber having a diameter of approximately 0.1 mm.

6. The endoscope system of claim 1, wherein said image path comprises optical grade plastic, said plastic coated with a light absorbent coating.

7. The endoscope system of claim 1, wherein said probe is substantially composed of plastic.

8. An endoscope system comprising:
   a xenon light source which emits pulses of high-energy light;
   an optical probe including a light pipe for transmitting said pulses of high-energy light to an area to be viewed and an image guide for transmitting light reflected from said area to be viewed to a location remote from said area, said image guide comprising a distal end which is inserted into the area to be viewed and an opposed proximal end, said image guide comprising a zoom optical system adjacent to the proximal end of said image guide; and
   optical transmission means for transmitting said pulses of high-energy light from said xenon light source to said optical probe.

9. The endoscope system of claim 8, wherein said optical probe has an outside diameter of less than 2 mm.

10. The endoscope system of claim 8, wherein said pulses of high energy light have a duration of less than 15 $\mu$-seconds.

11. The endoscope system of claim 8, wherein said xenon light source comprises:
    a xenon flash tube;
    an arcuate reflector; and
    an infra-red and ultra-violet light filter,
    said xenon flash tube being disposed between said arcuate reflector and said filter, whereby said pulses of high-energy light are reflected by said arcuate reflector through said filter.

12. The endoscope system of claim 8, wherein said system comprises:
    electronic imaging means for creating an electronic image from light reflected from said area to be viewed.

13. The endoscope system of claim 8, wherein said image guide has a diameter of less than 2 mm.

14. The endoscope system of claim 8, wherein said light pipe comprises a tube-like arrangement of optical fibers, each said optical fiber having a diameter of approximately 0.1 mm, said tube-like arrangement having a wall thickness of approximately 0.5 mm.

15. An endoscope system comprising:
    a xenon light source which emits pulses of high-energy light;
    an optical probe including a light pipe for transmitting said pulses of high-energy light to an optical area to be viewed and an image guide for transmitting light reflected from said area to be viewed to a location remote from said area, said light pipe comprising a tube-like molded structure including a core material having a high index of refraction and surrounding material having an index of refraction substantially lower than said core material; and
    optical transmission means for transmitting said pulses of high-energy light from said xenon light source to said optical probe.

16. The endoscope system of claim 15, wherein said image guide comprises a distal end which is inserted into the area to be viewed and an opposed proximal end, said image guide comprising a zoom optical system adjacent to the proximal end of said image guide.

17. The endoscope system of claim 16, wherein said zoom optical system provides multiple selectable zoom positions.

18. The endoscope system of claim 17, wherein said zoom optical system includes axially spaced lenses and mechanical means for altering the axial spacing of said lenses to achieve said multiple selectable zoom positions.

19. The endoscope system of claim 15, wherein said tube-like molded structure has an inside diameter of less than 2 mm and a wall thickness of approximately 0.1 mm.

* * * * *